(12) United States Patent
Fiedler et al.

(10) Patent No.: US 10,792,049 B2
(45) Date of Patent: Oct. 6, 2020

(54) ORTHOPAEDIC SURGICAL INSTRUMENT FOR POSITIONING A TIBIAL CUTTING GUIDE

(71) Applicant: LIMACORPORATE S.p.A., Villanova di San Daniele del Friuli (UD) (IT)

(72) Inventors: Christoph Fiedler, Diekhof (DE); Alessandra Bordon, San Pietro al Natisone (IT)

(73) Assignee: LIMACORPORATE S.P.A., San Daniele del Friuli (UD) (IT)

( * ) Notice: Subject to any disclaimer, the term of this patent is extended or adjusted under 35 U.S.C. 154(b) by 313 days.

(21) Appl. No.: 15/940,445

(22) Filed: Mar. 29, 2018

(65) Prior Publication Data

US 2018/0280031 A1 Oct. 4, 2018

(30) Foreign Application Priority Data

Apr. 3, 2017 (IT) .......................... 102017000036225

(51) Int. Cl.
*A61B 17/15* (2006.01)
(52) U.S. Cl.
CPC .................................. *A61B 17/157* (2013.01)
(58) Field of Classification Search
CPC ..... A61B 17/15; A61B 17/154; A61B 17/155; A61B 17/157
See application file for complete search history.

(56) References Cited

U.S. PATENT DOCUMENTS

| 5,578,039 | A | * | 11/1996 | Vendrely | A61B 17/157 |
| | | | | | 606/88 |
| 8,758,354 | B2 | * | 6/2014 | Habegger | A61B 17/157 |
| | | | | | 606/88 |
| 9,433,425 | B2 | * | 9/2016 | Wilkinson | A61F 2/4684 |
| 10,285,714 | B2 | * | 5/2019 | Branscome | A61B 17/157 |
| 2005/0187557 | A1 | | 8/2005 | Collazo | |

(Continued)

FOREIGN PATENT DOCUMENTS

| EP | 0 337 901 A1 | 7/2008 |
| WO | WO 2008/091358 A1 | 7/2008 |

*Primary Examiner* — Eric S Gibson
(74) *Attorney, Agent, or Firm* — Hickman Palermo Becker Bingham LLP; Malgorzata A. Kulczycka

(57) ABSTRACT

The invention relates to an orthopaedic surgical instrument (1) for positioning a tibial cutting guide (2) including:

at least a medial or a lateral cutting guide (3) and a vertical cutting guide (4) formed in a guide body (10);

an arm or beam (11) supporting said guide body (10);

a supporting rod (8) having a proximal end (18) coupled to said guide body (10) through said arm or beam (11). The arm (11) has a structure that is supported in a rotably and cantilever manner at the proximal end (18) of said rod (8);

a locking mechanism (20) is provided in the proximity of said proximal end (18) for locking the arm (11) in a desired position; and a bistable mechanical switch (9) is active in said locking mechanism (20) for manually activating the locking position.

In other words, the arm (11) has one end (17) hinged to the proximal end (18) of the supporting rod (8) between a terminal stopper (37) and a compressing element (31) slidably mounted in the proximity of said proximal end (18) and pushed toward the proximal direction by said bistable mechanical switch (9) of the locking mechanism (20).

30 Claims, 9 Drawing Sheets

(56) References Cited

U.S. PATENT DOCUMENTS

| | | | | |
|---|---|---|---|---|
| 2006/0241639 A1* | 10/2006 | Kuczynski | ........... | A61B 17/155 606/88 |
| 2007/0186738 A1* | 8/2007 | McGinley | ............ | A61B 17/157 83/88 |
| 2007/0233138 A1* | 10/2007 | Figueroa | .............. | A61B 17/155 606/87 |
| 2010/0331991 A1* | 12/2010 | Wilkinson | .............. | A61B 17/16 623/20.32 |
| 2012/0316563 A1* | 12/2012 | Metzger | ............. | A61B 17/1764 606/80 |
| 2013/0116698 A1* | 5/2013 | Wilkinson | ........... | A61B 17/157 606/88 |
| 2013/0204260 A1* | 8/2013 | Dietzel | ................ | A61B 17/157 606/88 |
| 2014/0066934 A1* | 3/2014 | Deirmengian | ..... | A61B 17/1764 606/83 |
| 2015/0173781 A1* | 6/2015 | Metzger | ............. | A61B 17/1764 606/88 |
| 2017/0135708 A1* | 5/2017 | Jaumard | ............ | A61B 17/1764 |
| 2018/0070960 A1* | 3/2018 | Branscome | ........... | A61B 17/157 |
| 2018/0070961 A1* | 3/2018 | Branscome | ........... | A61B 17/155 |
| 2018/0280031 A1* | 10/2018 | Fiedler | ............... | A61B 17/1764 |
| 2019/0269422 A1* | 9/2019 | Metzger | .................. | A61F 2/461 |
| 2019/0290293 A1* | 9/2019 | Branscome | .......... | A61B 17/157 |

* cited by examiner

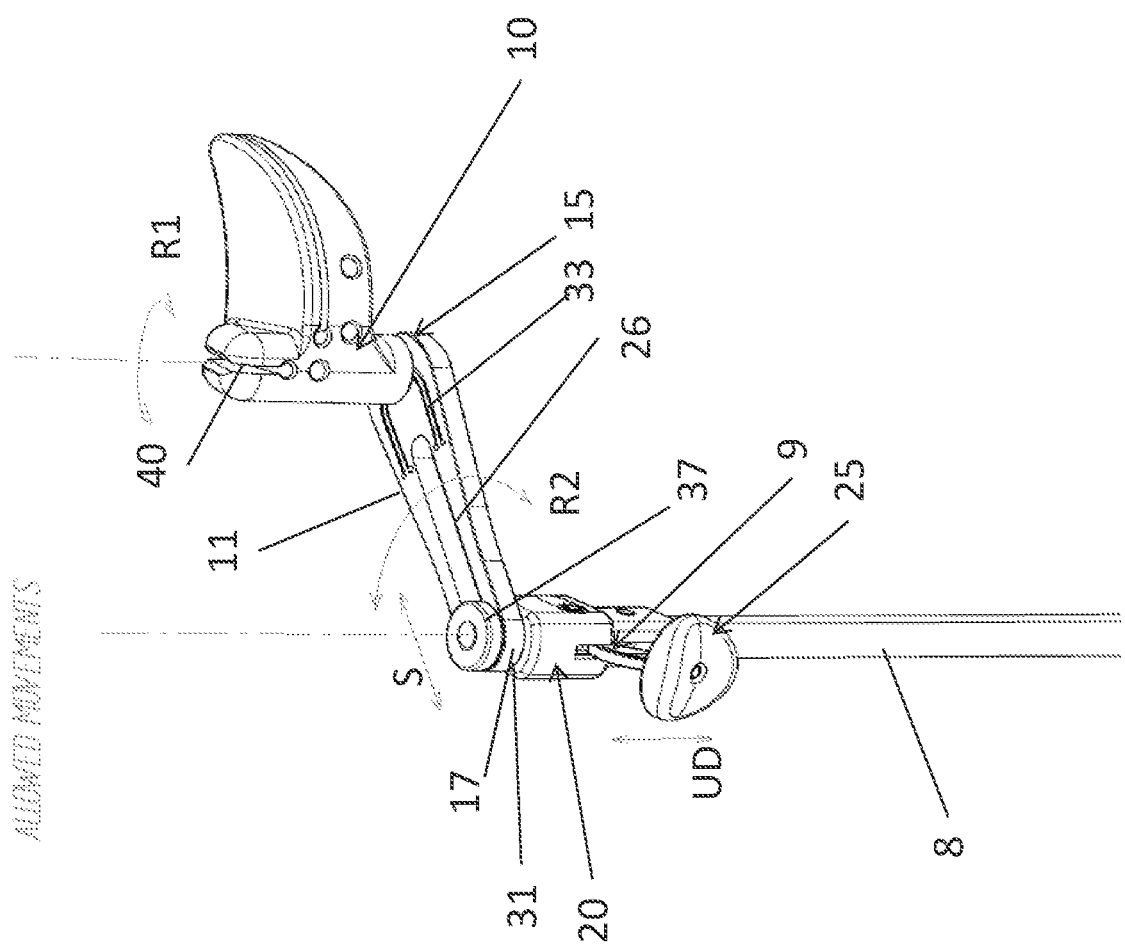

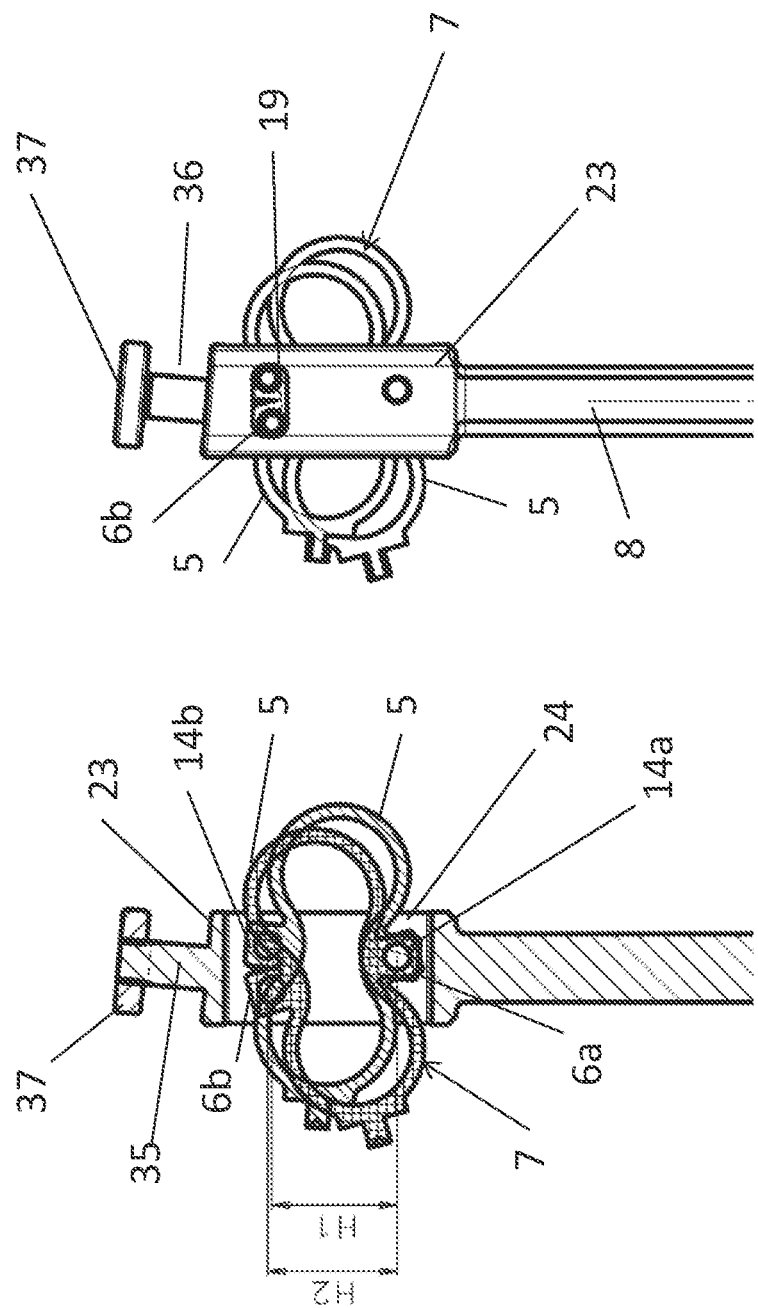

ORTHOPAEDIC SURGICAL INSTRUMENT FOR POSITIONING A TIBIAL CUTTING GUIDE

BENEFIT CLAIM

This application claims the benefit of Italy application 102017000036225, filed Apr. 3, 2017, the entire contents of which are hereby incorporated by reference for all purposes as if fully set forth herein, under 35 U.S.C. § 119.

DESCRIPTION

Technical Field

The present invention relates to an orthopaedic surgical instrument for positioning a tibial cutting guide.

More particularly, but not exclusively, the invention relates to an orthopaedic surgical instrument including:
- at least a medial or a lateral cutting guide and a vertical cutting guide formed in a guide body;
- an arm or beam supporting said guide body;
- a supporting rod having a proximal end coupled to said guide body through said arm or beam.

As is well known in this specific technical field, the tibia is the second largest bone in human anatomy and is located next to the femur. More specifically, the tibia is one of two bones in the lower leg, the other being the fibula, and is a component of the knee and ankle joints.

The tibia is a long bone and is as such composed of a diaphysis and two epiphyses. The diaphysis is the midsection of the tibia also known as shaft or body. While the epiphyses are the two rounded extremities of the bone; an upper (also known as superior or proximal) closest to the thigh and a lower (also known as inferior or distal) closest to the foot. The tibia is most contracted in the lower third and the distal extremity is smaller than the proximal The proximal or upper extremity of the tibia is expanded in the transverse plane with a medial and lateral condyle, which are both flattened in the horizontal plane. The medial condyle is the largest of the two and is better supported over the shaft. The upper surfaces of the condyles articulates with the femur to form the tibiofemoral joint, that is to say: the weight bearing part of the knee joint.

Known Art

Now, in many treatments of the knee joint there is the need to resect the patient's proximal tibia for installing a knee prosthesis.

In knee joint replacement surgery, a surgeon typically affixes two prosthesis components to the patient's femur and tibia. These replacement components are typically known as the femoral component and the tibial component.

Commonly a total knee prosthesis is used for replacing both sides, lateral and medial, after the proximal tibia has been cut transversely by the surgeon. A plastic polymeric insert is generally attached to the tibial tray to provide an articulating surface.

In case that only one compartment is damaged, the surgeon can chose a unicondylar prosthesis. In this case only the medial (or the lateral) part of the tibia will be cut by the surgeon and an additional horizontal cut has to be done in order to separate the both condyles. This horizontal cut depends on the patient's anatomy and needs to be adapted in position and orientation for every patient.

To help the surgeon in his task the known art offers system and devices for bone resection such as the tibial resection instrument disclosed in EP 0 809 468 B1 to Smith & Nephew or the system for tibial resection disclosed in EP 2 032 046 always to Smith & Nephew.

Those instruments provide for tibial resection guides that are supported in the proximity of the proximal tibial epiphyses to limit the cutting instrument in the transverse plane.

A first medial resection guide is generally supported by an arm and is associated to a second lateral resection guide; both guides are configured to cut a portion of the tibial condyles, respectively.

However, when it is necessary to cut only one condyle portion there is a real risk to cut more than necessary and even to resect the knee ligaments.

Another prior art solution is disclosed in the US patent application No. 2013/204260 A1 disclosing an apparatus with a cut guide including a locking area, an alignment guide, and a connect mechanism to connect the cut guide to the alignment guide; in such an apparatus the connect mechanism includes a cone lock connect mechanism configured to engage with the cut guide locking area.

Unfortunately, even if the prior art solutions may be considered advantageous under many aspects, they are still rigid in their supporting structure and have no enough freedom of configuration to allow performing a cut without risk, in particular when only one condyle portion is to be treated.

The technical problem at the basis of the present invention is that of providing an orthopaedic surgical instrument for positioning a tibial cutting or resection guide according to the anatomy of the patient and to fix the cutting guide in the desired position with a very quick manual action that may be performed with a single finger of the surgeon thus overcoming all the limitations of the known art solutions.

Another aim of the present invention is that of providing a support for a tibial cutting or resection guide having only few components allowing the fixation of the cutting position in a very simple and reliable manner.

A further aim of the present invention is that of providing an orthopaedic surgical instrument having structural and functional features to allow a fast adjustment of the positioning of the tibial cutting guide according to the surgeon needs after the knee has been surgically exposed.

A further aim of the present invention is that having a correct positioned cutting guide for both cuts (horizontal and vertical) a pin can be used at the intersection of both cuts to prevent overcutting.

SUMMARY OF THE INVENTION

The solution idea at the basis of the present invention is that of supporting the tibial cutting guide in a rotably and cantilever manner with respect to top proximal end of the orthopaedic instrument and to lock the desired positioning with a releasable fixing mechanism that may be activated by a single finger of the surgeon hand.

According to this inventive solution the technical problem is solved by an orthopaedic surgical instrument according to the preamble of claim 1 and characterized by comprising:
- an arm structure supported in a rotably and cantilever manner at the proximal end of said rod;
- a locking mechanism in the proximity of said proximal end for locking the arm in a desired position;
- a bistable mechanical switch in said locking mechanism for manually activating the locking position.

Advantageously, the mentioned arm structure includes a longitudinal slot extended along a portion of the arm and engaged by an annular recess formed at the proximal end of said rod for supporting the arm is a slidable, rotable and cantilever manner with respect to said proximal end of said rod.

Moreover, the mechanical switch of said locking mechanism includes an elastic element associates to a command button and movable between a rest position and an active position wherein it pushes a slidable element in abutment against said arm thus locking its position.

Said in other words, the arm structure has one end hinged to the proximal end of the supporting rod between a terminal stopper (37) and a compressing element slidably mounted in the proximity of said proximal end and pushed in the toward the proximal direction by said bistable mechanical switch of the locking mechanism.

The compressing element is the bottom wall of a sort of sleeve or reversed cup that is leant and slidably mounted on an enlarged portion of said proximal end and having a central hole allowing the passage of a top cylindrical portion of the proximal end.

More specifically, the longitudinal slot of said arm is engaged by a cylindrical portion defined by said annular recess between an enlarged portion of the proximal end of said rod and a stopper.

It should be noted that said cylindrical portion has an axis inclined of few degrees with respect to the main axis of the supporting rod.

The mechanical switch of the locking mechanism includes an elastic element associated to an activation button and moveable between a rest position and an active position wherein the position of said arm is locked by a compression action.

More particularly, said elastic element is hosted in a slot formed in the proximal end of said rod and said activation button projects outside said slot.

The elastic element comprises an eight shaped spring having opposite rounded ends projecting outside the slot formed in the proximal end and the activating command is linked to one rounded end of the eight shaped spring.

There are a couple of flanges formed in the restricted portion of the eight shaped spring to support corresponding transversal pins; one pin being pivotable in a hole formed transversally in said slot with the other pin being free to slide inside a transversal slot of the same said slot in order to move the elastic element from a rest to an active stable position that is a consequence of the deformation of the said elastic element.

In more details, the arm structure is embossed with a first end coupled to the top proximal end of the supporting rod and the opposite end forming a fork like gripping end portion embracing an annular slot of a supporting pin formed in said guide body.

The opposite end of the arm is larger and rounded if compared to the first end and a double cut is provided in fork like gripping end portion to assure an elastic locking connection of the cutting guide.

The longitudinal elongated slot is realized along the arm structure for about two thirds of its length starting in the proximity of the first end.

A selected embodiment will now be explained with reference to the enclosed drawings. It will be apparent to those skilled in the orthopaedic field from this disclosure that the following descriptions of the embodiment is provided for illustration only and not for the purpose of limiting the invention as defined by the appended claims and their equivalents.

BRIEF DESCRIPTION OF THE DRAWINGS

FIGS. 7 and 8 are schematic perspective view of the proximal portion of the instrument of the invention in two different configurations, locked and unlocked, respectively;

FIG. 9 is a schematic cross sectional view of the proximal portion of the instrument of the invention showing in a same figure two different positions of a structural feature of the invention;

FIG. 10 is a schematic lateral view of the proximal portion of the instrument of the invention showing in a same figure two different positions of a structural feature of the invention;

DETAILED DESCRIPTION

Figure 1:
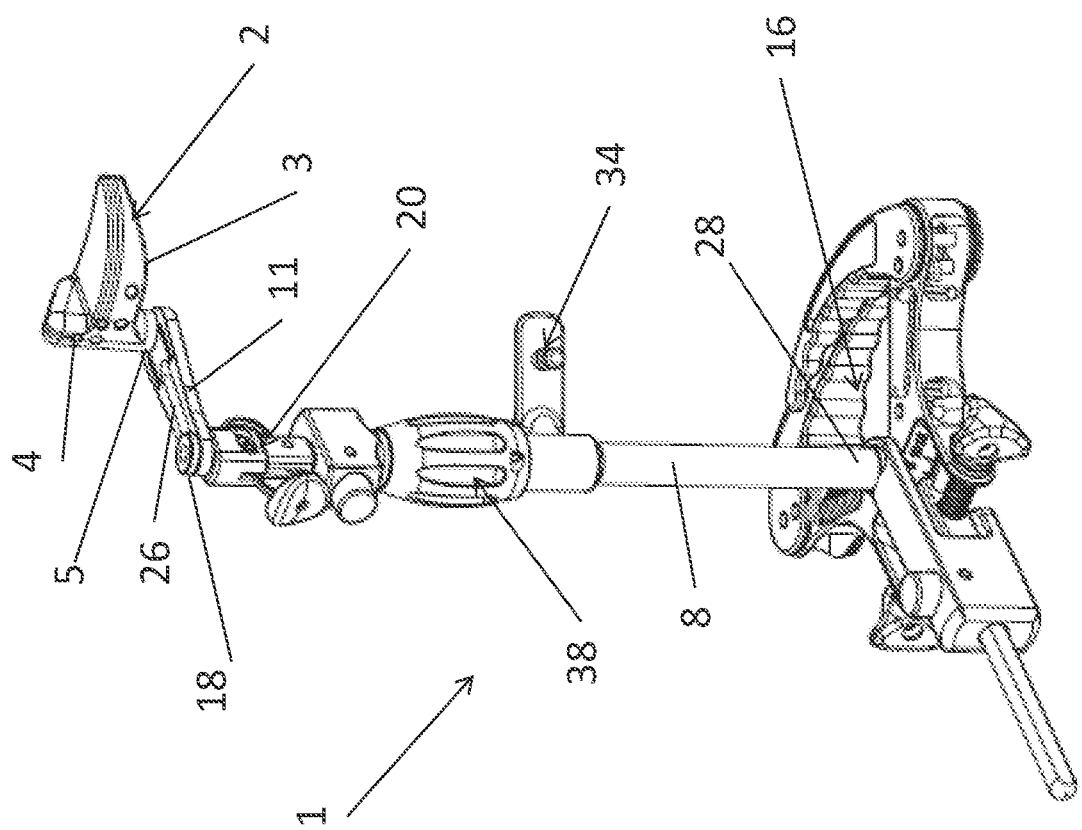
FIG. 1 is a schematic and perspective view of an orthopaedic surgical instrument realized according to the present invention.
Figure 2:
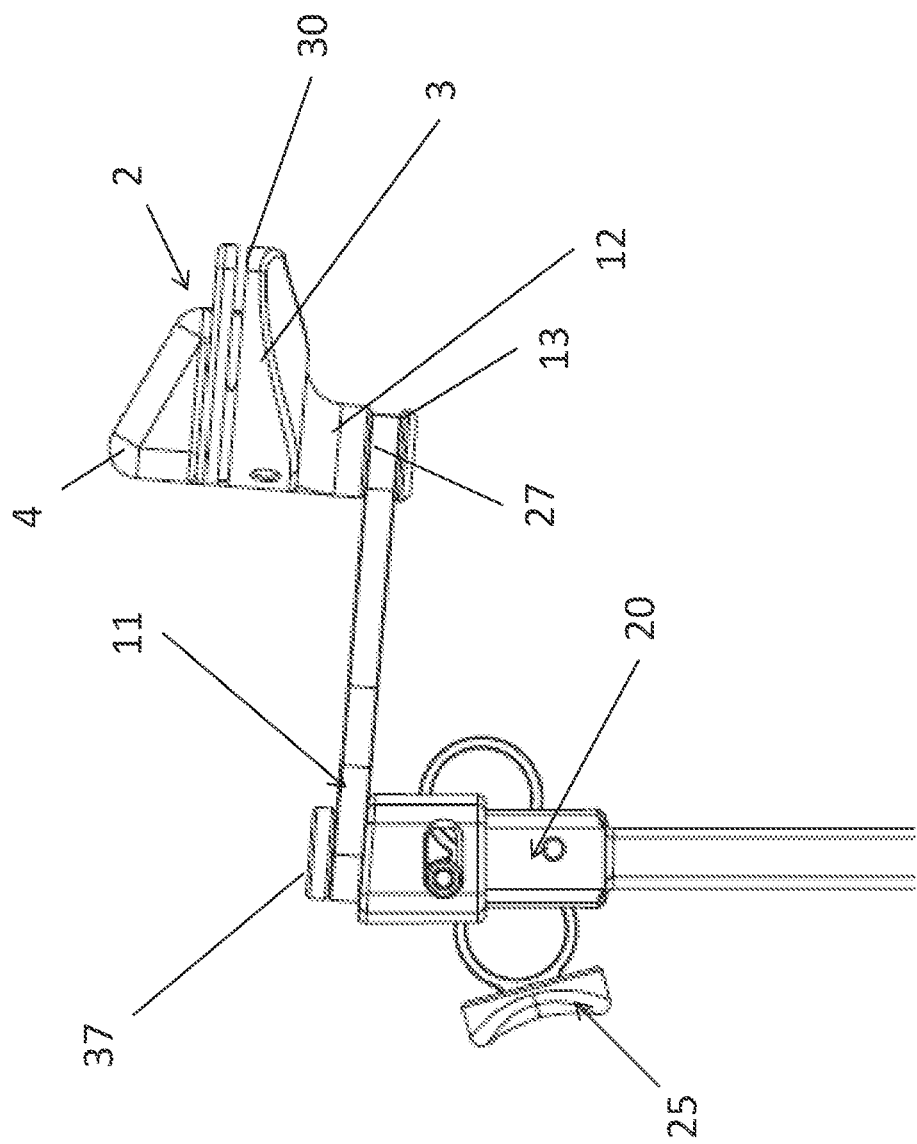
FIG. 2 is a schematic and lateral view of a particular of the instrument of FIG. 1.
Figure 3:
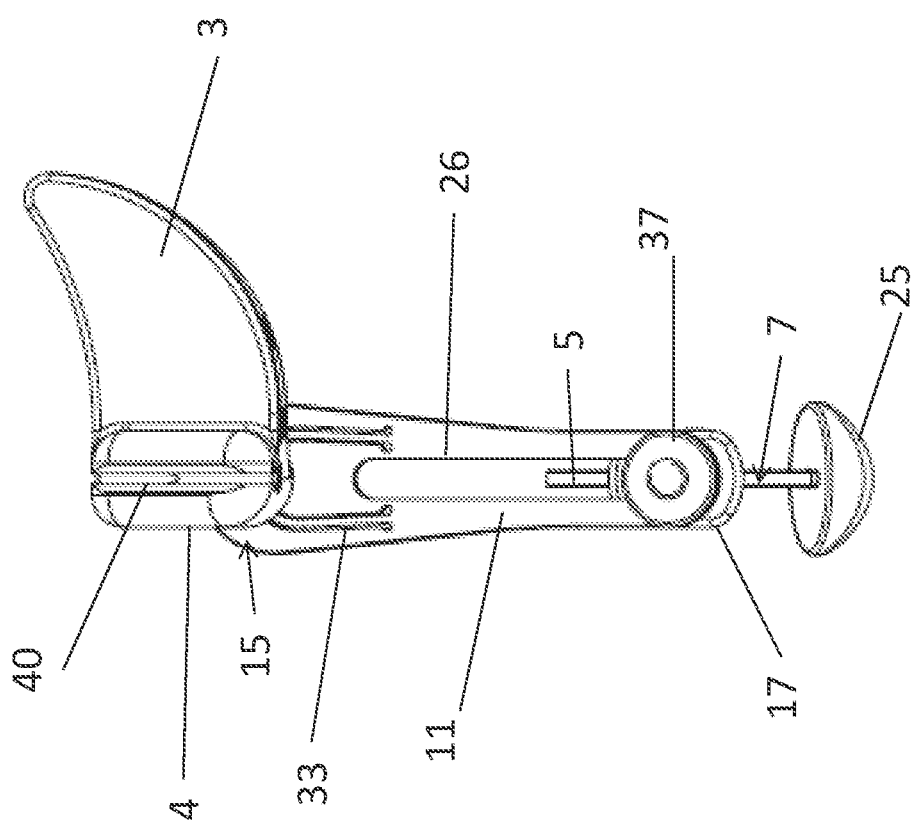
FIG. 3 is a top view of the proximal portion of the orthopaedic instrument realized according to the invention.

With reference to the enclosed drawings figures, with 1 is globally and schematically shown an orthopaedic surgical instrument realized according to the present invention for positioning a tibial cutting or resection guide 2.

The structure of the orthopaedic surgical instrument realized according to the present invention allows a fast adjustment of the positioning of the tibial guide according to the surgeon needs and after the knee has been surgically exposed.

Advantageously, the tibial guide 2 is supported in a rotably and cantilever manner at the proximal end of the instrument 1 in the proximity of a patient's proximal tibia, as will be apparent from the following of the disclosure.

Generally speaking, the instrument 1 comprises an extramedullary (EM) supporting rod 8 that is extended parallel to the tibial diaphysis during the use of the instrument and has a distal end 28 coupled to an ankle clamp 16.

The ankle clamp 16 is of a conventional type and is not part of the present invention. Many different and alternative ankle clamps may be employed with the instrument of the present invention and a detailed description of the structure and functioning of the ankle clamp showed in the drawings will be omitted not to extend the present disclosure.

Advantageously, according to the present invention, the instrument 1 includes a quick activating mechanism 20 for positioning and fixing the tibial guide 2 according to the surgeon needs. The structure and functioning of this quick activating mechanism 20 will be disclosed in great details hereinafter.

Coming back to the tibial resection guide 2, it should be noted that it includes at least a lateral cutting guide 3 and a vertical cutting guide 4 that is extended perpendicularly or orthogonally with respect to the lateral cutting guide 3. With the term "lateral" we will define a guide for cutting the lateral condyle.

In many embodiments of the known art the tibial resection guide includes both a medial cutting guide (i.e. a guide for cutting the medial condyle) and a lateral cutting guide, with or without corresponding vertical cutting guides.

In the preferred embodiment of the present invention we will take in consideration an example wherein only one of the medial and lateral cutting guide is present, i.e. the lateral cutting guide 3.

However, it should be noted that the invention may be applied independently to one or the other of those medial or lateral cutting guides. Therefore, in the following description we will refer to the lateral cutting guide 3 with the only purpose to simplify the invention disclosure but not with the intent to limit the applicant's right.

The lateral and vertical cutting guides 3 and 4 comprise corresponding slots 30 and 40 and are supported by a guide body 10. More specifically, the cutting guides 3, 4 are formed integrally in said guide body 10.

A supporting cylindrical portion 12 is formed at a corner of the guide body 10 in substantial alignment with the vertical guide 4 but projecting toward the distal direction.

This cylindrical portion 12 has a circular indentation 13 that is engaged by a gripping end portion 15 of a supporting arm 11 or beam extended in a cantilever manner from the top proximal end 18 of the extra-medullary (EM) rod 8.

The gripping end portion 15 is shaped substantially as an elastic fork to allow a fast insertion or substitution of the guide body 10 into the circular indentation 13 of the cylindrical portion 12; however, many other alternative gripping ends may be adopted, for instance a couple of clamps.

The arm 11 structure is captured with a first end 17 coupled to the top proximal end 18 of the supporting rod 8 and the opposite end 27 forming the gripping end portion 15 embracing the circular indentation 13 of the cylindrical portion 12.

A longitudinal elongated slot 26 is realized along the arm 11 structure for about two thirds of its length starting in the proximity of the first end 17. The position and the length of the slot is exemplary without the intent to limit the applicant's right.

The opposite end 27 is larger and rounded if compared to the first end 17 of the arm 11. A double cut 33 is provided in fork like gripping end portion 15 to guarantee the elasticity of the whole gripping structure.

The length of this double cut 33 is defined by the predetermined chosen force of the gripping end portion 15. This double cut 33 runs starting from the approximate center of the arm 11 following substantially the external profile until the gripping end portion 15.

Figure 7:
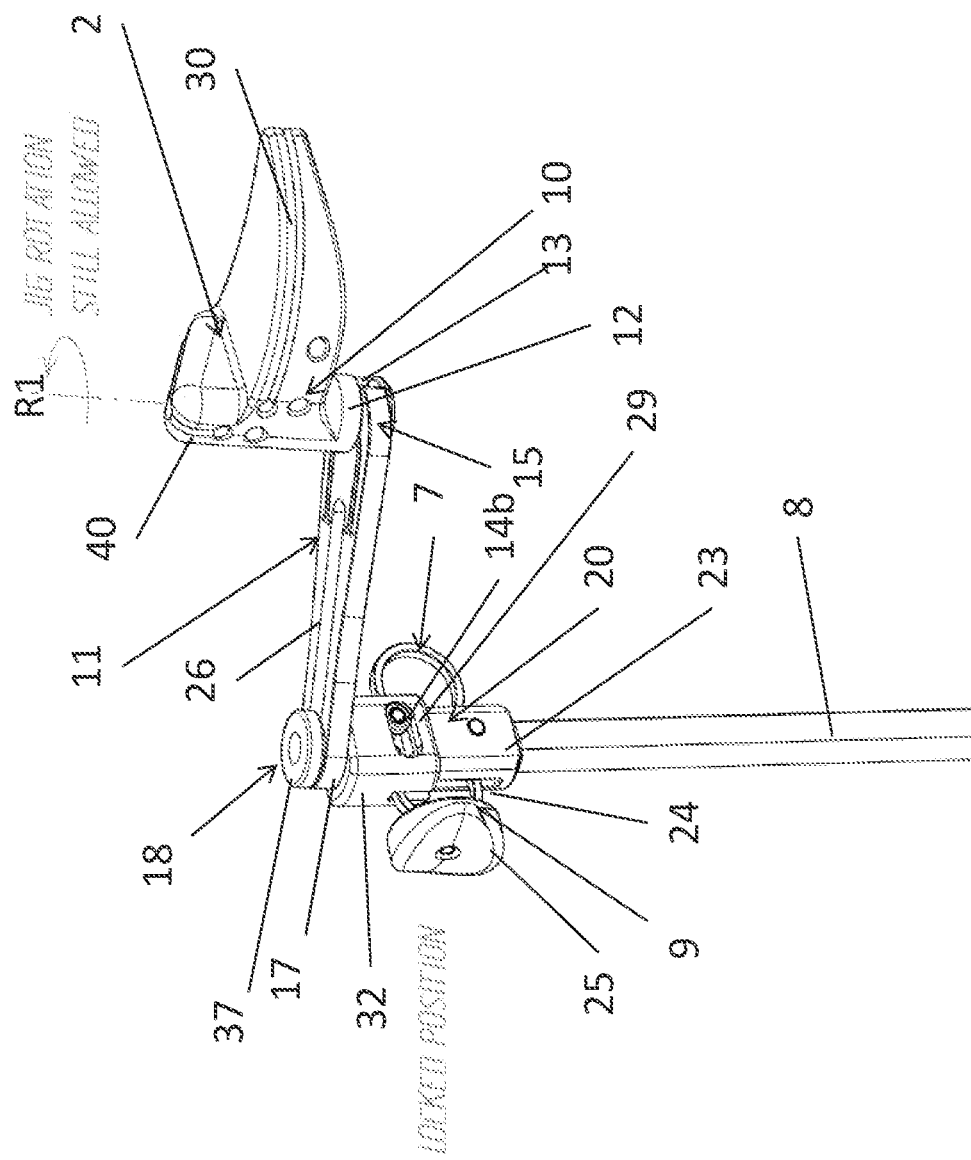

The arm structure so configured allows the guide body 10 to be rotably around the vertical axis of the cylindrical portion 12 as shown by the arrow R1 in FIGS. 7 and 8. An annular recess 36 is provided in proximity of the top proximal end 18 of the supporting rod 8 so that the top terminal of the proximal end 18 may be defined as a stopper 37. This stopper 37 may be a cap screwed on the proximal end 18.

The annular recess 36 is slidable inside the slot 26 of the arm 11 structure allowing the arm 11 to be supported in a cantilever manner but in a position that may be more or less extended with respect to the top proximal end 18 of the rod 8. FIG. 8 reports this possible cantilever extension as a possible movement in the direction of the arrow S.

It should be further noted that this annular recess 36 delimits a cylindrical portion 35 that is slightly inclined of few degrees and more specifically of an angle $\alpha$ of about 5° with respect to the longitudinal axis of the supporting rod 8.

This inclination depends on the implant design.

At the same time, the coupling between the cylindrical portion 35 of the annular recess 36 and the slot 26 allows the arm 11 to be rotably mounted around the top proximal end 18 of the rod 8, under the stopper 37, as shown by the arrow R2 in FIG. 8.

In other words, the arm 11 may be rotable and at the same time may be extended in a cantilever manner with respect to top proximal end 18 of the orthopaedic instrument 1. This arm 11 may be locked and fixed in the desired position thanks to an action on the releasable fixing mechanism 20 activated by a single finger of the surgeon hand.

Let's now focus our attention of the quick activating locking mechanism 20 that is provided at the proximal end 18 of the EM supporting rod 8.

The locking mechanism 20 is hosted in a passing slot 24 provided in an enlarged portion 23 of the proximal end 18 of the supporting rod 8.

The slot 24 may be defined as axial in the sense that it is extended for a predetermined axial length of the proximal end 18, corresponding substantially to said enlarged portion 23, and is open on both sides of the enlarged portion 23.

A transversal hole 19 is provided inside the slot 24 as well as a transversal slot 29. This transversal slot 29 works as stop for the bi-stable mechanical switch 9 limiting the extension of the elastic element 7 for both positions.

A bistable mechanical switch 9 is hosted inside the passing slot 24 with an activating command or button 25 projecting laterally outside the slot 24.

More specifically, said bistable mechanical switch 9 comprises an elastic element 7 having a particular configuration with a main eight shaped spring 5 having opposite rounded ends projecting outside the slot 24.

Said activating command or button 25 is linked to one rounded end of the eight shaped spring 5.

A couple of flanges 6a, 6b are formed in the restricted portion of the eight shaped spring 5 to support corresponding transversal pins 14a, 14b.

One pin 14a is pivotable in the hole 19 while the other pin 14b is free to slide inside the slot 29 to move from one stable end position of this slot 29 to the other stable opposite end position.

In this manner the eight shaped spring 5 is moveable between two stable positions activated by a manual action, or better by a single finger action, on the command or button 25, as shown in FIGS. 4 and 5 or FIGS. 7 and 8.

A sort of sleeve or reversed cup 32 is leant and slidably mounted on the top of the enlarged portion 23 of the proximal end 18. This cup 32 has a upper wall 31 with a central hole allowing the passage of the top cylindrical portion 35 of the proximal end 18. Without considering the presence of the arm 11, the sleeve 32 will move up and down by pressing the mechanical bi-stable switch 9. With the arm 11 in place, the sleeve 32 will be pressed against the arm in the locked position while there is a small clearance when the switch is in the unlocked position.

In this manner the arm 11 is trapped in the recess 36 between the stopper 37 and the wall 31 of the reversed cup 32.

The sleeve or reversed cup 32 has opposite opening slots corresponding to the slot 24 and allowing the passage of the opposite rounded ends of the eight shaped spring 5.

The quick activating locking mechanism 20 of the present invention operated as follows.

The whole structure of the tibial resection guide 2, the cantilever arm 11 and the locking mechanism 20 assures a stable positioning of the tibial guide body 10 against or in front of the tibia to be cut.

The inclined cylinder portion 35 allows the correct positioning of the tibial guide body 10 according to the implant geometries.

The surgeon has the possibility to adjust the positioning of the tibial guide according to the intervention needs and to lock the desired and reached position acting with a single hand and with a finger of this hand.

A manual action on the button 25 switches the position of the mechanical switch 9 from the rest and release position shown for instance in FIG. 8 to a locked position shown in FIG. 7.

Acting on the button 25 the spring 5 is switched in the lock position that interferes with the sleeve or cup element 32 that can normally be moved vertically along the direction UD (Up-Down) for a short excursion.

In the locked position the arm 11, normally free to move rotating and sliding around the cylindrical portion 35, is compressed between the stopper 37 and the wall 31 of the cup 32 being stopped in the desired position.

The elastic element 7 of the mechanical switch 9 has substantially two working positions:

Position 1: the elastic element 7 is relaxed and the sleeve or cup 32 remains stationary, allowing the arm 11 to move freely in the modest clearance between the stopper 17 and upper wall 31 of the cup 32.

Position 2: the elastic element 7 is compressed, moving the cup 32 vertically and pressing it against the arm 11, reducing all the existing clearance and fixing the position of the arm 11.

By pulling down the button 25 of the elastic element 7 the mechanism 20 is released unlocking the arm 11 and allowing a repositioning of the guide body 10.

In FIG. 9 it is shown in a schematic manner the short excursion between the first position wherein a distance H1 is defined between the pin 6a and the other pin 6b sliding in the slot 29.

In the second and locked position the distance H2 between the above pins 6a and 6b is slightly greater because of the angular position of the opposite end of the slot 29 with respect to the hole 19 hosting the pin 6a.

This modest difference H2-H1 of about half a mm produces a compression of the elastic element 7, according to the properties of the elastic element (i.e. the spring 5), and a visible raising effect on the rounded shape of the sprig 5 projecting outside the slot 24 at the side of the button 25.

This effect pushes the sleeve or cup 32 in abutment against the hinged end 17 of the arm 11 and against the stopper 37.

Once the position of the arm 11 is decided and locked, one more degree of freedom is still available to guide body 10 for instance the rotation around its vertical axis, perpendicularly to the plane of arm 11, as shown in FIG. 7. This feature allows the surgeon to place the guide body 10 in the most correct place to perform a perfect cut. Optional a pin can be inserted into the bone at the intersection of both cuts to prevent the saw blade going too deep into the bone. For completeness of disclosure it should be noted that the whole proximal portion of the orthopaedic instrument of the present invention may be optionally removed from the supporting rod 8 once the guide body has been correctly positioned and secured to the bone via pins.

Figure 4:
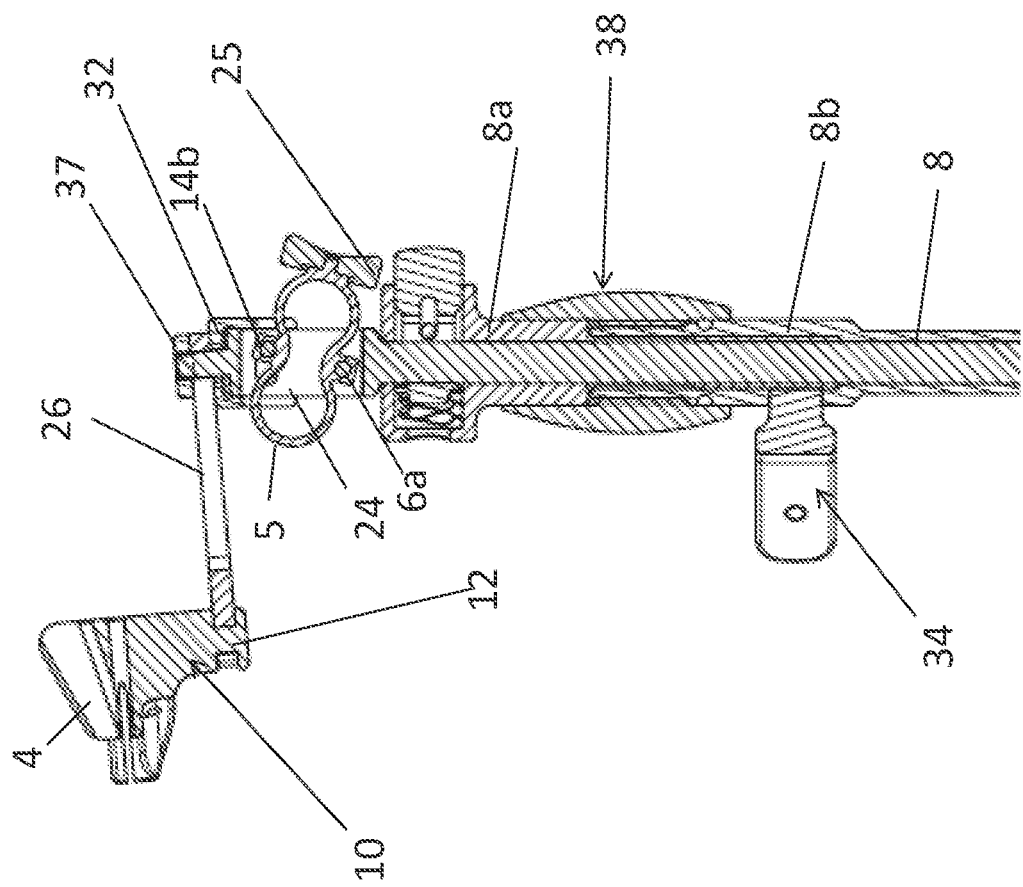
FIG. 4 is a cross sectional view, taken along the vertical plane, of the particular of FIG. 2 in a first positioning and functioning configuration, wherein the arm is disengaged and free to move.
Figure 5:
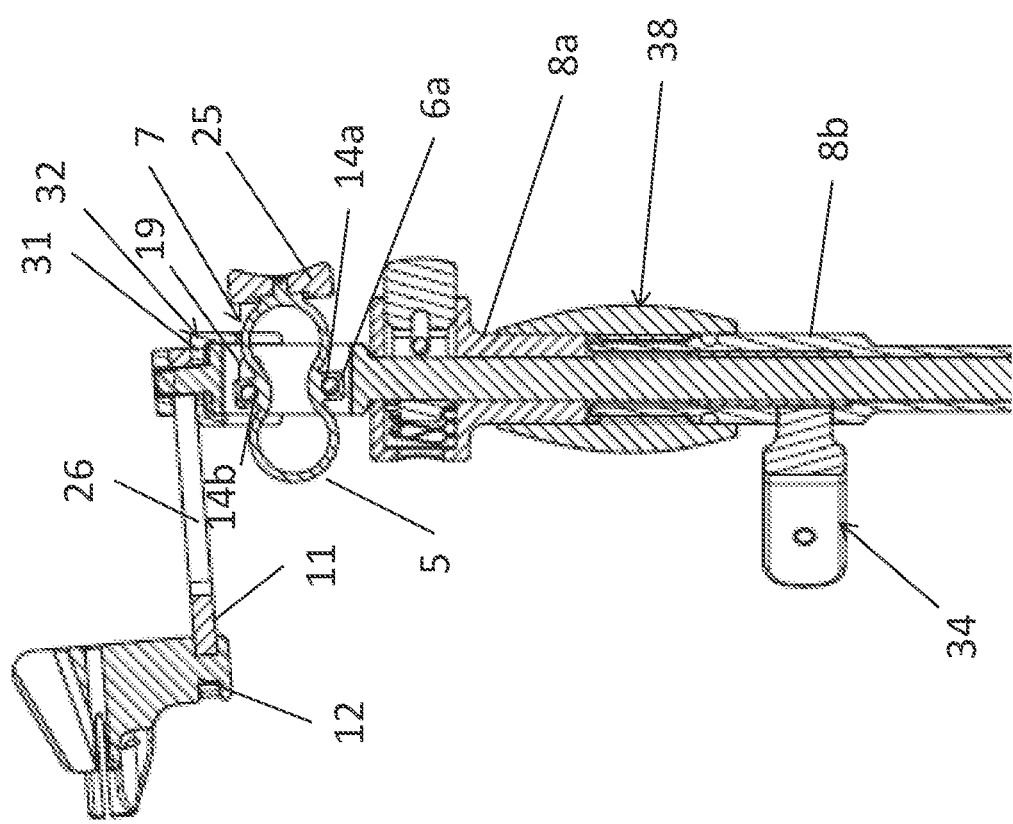
FIG. 5 is a cross sectional view, taken along the vertical plane, of the particular of FIG. 2 in a second positioning and functioning configuration, wherein the arm position is locked.
Figure 6:
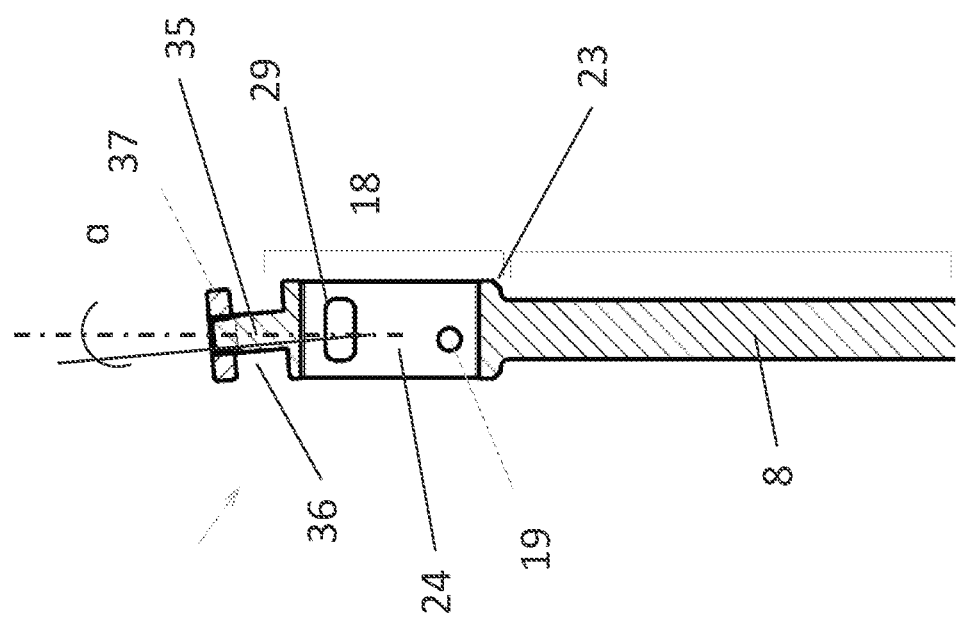
FIG. 6 is a schematic cross sectional view of a particular of the proximal portion of the instrument of the invention.

In FIGS. 1, 4 and 5 it is also shown an embodiment wherein the upper and proximal portion of the instrument 1 may be telescopically adapted to the length of the patient's leg. In this respect a knob 38 is provided with an internal tread for engaging the facing ends of two portions 8a and 8b covering in a sliding manner the supporting rod 8.

The more distal portion 8b has lateral flanges 34 provided to ensure a stable position of the instrument to the tibial bone. From the previous description it is evident for a skilled in the art that the invention solves the technical problem and reaches a number of advantages the most important of which is the great freedom allowed to the surgeon in positioning the tibial resection guide during the delicate intervention phase and fixing it.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts unless otherwise stated.

Also it will be understood that although the terms "first" and "second" may be used herein to describe various components these components should not be limited by these terms. These terms are only used to distinguish one component from another.

While only selected embodiments have been chosen to illustrate the present invention, it will be apparent to those skilled in the art from this disclosure that various changes and modifications can be made herein without departing from the scope of the invention as defined in the appended claims.

The invention claimed is:

1. An orthopaedic surgical instrument for positioning a tibial cutting guide including:
   at least a medial or a lateral cutting guide and a vertical cutting guide formed in a guide body;
   an arm or beam supporting said guide body;
   a supporting rod having a proximal end coupled to said guide body through said arm or beam;
   said arm or beam having a structure being supported in a rotatably and cantilever manner at the proximal end of said supporting rod;
   a locking device in proximity of said proximal end of said supporting rod, said locking device being configured for locking the arm or beam in a desired locking position;
   wherein the locking device comprises a mechanical switch configured for manually activating the desired locking position.

2. The orthopaedic surgical instrument according to claim 1, wherein said structure of the arm or beam includes a longitudinal slot extended along a portion of the arm or beam and engaged by an annular recess formed at the proximal end of said supporting rod in a slidable, rotatable and cantilever manner with respect to said proximal end of said supporting rod.

3. The orthopaedic surgical instrument according to claim 2, wherein said longitudinal slot of said arm or beam is engaged by a cylindrical portion defined by said annular recess between an enlarged portion of the proximal end of said supporting rod and a stopper.

4. The orthopaedic surgical instrument according to claim 3, wherein said cylindrical portion has an axis inclined with respect to a main axis of the supporting rod.

5. The orthopaedic surgical instrument according to claim 3, wherein said slot is formed in an enlarged portion of said proximal end of said supporting rod and is open on both sides of said enlarged portion.

6. The orthopaedic surgical instrument according to claim wherein said structure of the arm or beam is embossed with a first end coupled to a top portion of the proximal end of the supporting rod and a second end opposite to said first end forming a fork-like gripping end portion embracing an annular slot of a supporting pin formed in said guide body.

7. The orthopaedic surgical instrument according to claim 6, wherein said second end of the arm or beam is larger and more rounded than the first end and a double cut is provided in fork-like gripping end portion to improve an elasticity of a gripping structure.

8. The orthopaedic surgical instrument according to claim 6, wherein said longitudinal slot is elongated and provided along the structure of the arm or beam for substantially two thirds of its length starting in proximity of the first end.

9. The orthopaedic surgical instrument according to claim 1, wherein said mechanical switch of said locking device includes an elastic element associated with a command button and movable between a resting position and an active position wherein the elastic element pushes a slidable element in abutment against said arm or beam.

10. The orthopaedic surgical instrument according to claim 1, wherein said mechanical switch of the locking device includes an elastic element associated with an activation button and moveable between a resting position and an active position wherein said arm or beam is locked by a compression action of said elastic element.

11. The orthopaedic surgical instrument according to claim 10, wherein said elastic element is hosted in a slot formed in the proximal end of said supporting rod and said activation button projects outside said slot.

12. The orthopaedic surgical instrument according to claim 10, wherein said elastic element comprises an eight shaped spring having opposite rounded ends projecting outside a slot of said proximal end of said supporting rod and said activation button is linked to one rounded end of the eight shaped spring.

13. The orthopaedic surgical instrument according to claim wherein a couple of flanges are formed in a narrower central portion of the eight shaped spring to support corresponding transversal pins; one pin being pivotable in a hole of said slot with the other pin being free to slide inside a transversal slot of said slot for moving the elastic element from a resting position to an active stable position.

14. The orthopaedic surgical instrument according to claim 1, wherein said arm or beam has one end hinged to the proximal end of the supporting rod between a terminal stopper and a slidable element slidably mounted in proximity of said proximal end of said supporting rod and configured for being pushed toward a proximal direction by said mechanical switch of the locking device, thus compressing the one end of said arm or beam.

15. The orthopaedic surgical instrument according to claim 14, wherein said slidable element is a bottom wall of a cylindrical sleeve or reversed cup that is in contact with and slidably mounted on an enlarged portion of said proximal end of said supporting rod and having a central hole allowing passing of a top cylindrical portion of the proximal end of said supporting rod.

16. An orthopaedic surgical instrument for fast adjustment of positioning of a tibial cutting guide including:
at least a medial or a lateral cutting guide and a vertical cutting guide formed in a guide body;
an arm or beam supporting said guide body including a longitudinal slot;
a supporting rod having a proximal end coupled to said guide body through said arm or beam; said arm or beam having a structure being supported in a rotatably and cantilever manner at the proximal end of said supporting rod;
a quick activating locking device in proximity of said proximal end of said supporting rod, said locking device being configured for locking the arm or beam in a desired locking position;
wherein the locking device comprises a mechanical switch configured for manually activating the desired locking position.

17. The orthopaedic surgical instrument according to claim 16, wherein said longitudinal slot of said arm or beam is engaged by a cylindrical portion defined by an annular recess between an enlarged portion of the proximal end of said supporting rod and a stopper.

18. The orthopaedic surgical instrument according to claim 17, wherein said cylindrical portion has an axis inclined with respect to a main axis of the supporting rod.

19. The orthopaedic surgical instrument according to claim 17, wherein said longitudinal slot is extended along a portion of the structure of the arm or beam and is engaged by said annular recess formed at the proximal end of said supporting rod for supporting the arm or beam in a slidable, rotatable and cantilever manner with respect to said proximal end of said supporting rod.

20. The orthopaedic surgical instrument according to claim 16, wherein said mechanical switch of said locking device includes an elastic element associated with a command button and movable between a resting position and an active position wherein the elastic element pushes a slidable element in abutment against said arm or beam.

21. The orthopaedic surgical instrument according to claim 16, wherein said mechanical switch of the locking device includes an elastic element associated with an activation button and moveable between a resting position and an active position wherein said arm or beam is locked by a compression action of said elastic element.

22. The orthopaedic surgical instrument according to claim 21, wherein said elastic element is hosted in a slot formed in the proximal end of said supporting rod and said activation button projects outside said slot.

23. The orthopaedic surgical instrument according to claim 22, wherein said slot is formed in an enlarged portion of said proximal end of said supporting rod and is open on both sides of said enlarged portion.

24. The orthopaedic surgical instrument according to claim 21, wherein said elastic element comprises an eight shaped spring having opposite rounded ends projecting outside a slot of said proximal end of said supporting rod and said activation button is linked to one rounded end of the eight shaped spring.

25. The orthopaedic surgical instrument according to claim 24, wherein a couple of flanges are formed in a narrower central portion of the eight shaped spring to support corresponding transversal pins; one pin being pivotable in a hole of said slot with the other pin being free to slide inside a transversal slot of said slot for moving the elastic element from a resting position to an active stable position.

26. The orthopaedic surgical instrument according to claim 16, wherein said structure of the arm or beam is embossed with a first end coupled to a top portion of the proximal end of the supporting rod and a second end opposite to said first end forming a fork-like gripping end portion embracing an annular slot of a supporting pin formed in said guide body.

27. The orthopaedic surgical instrument according to claim 26, wherein said second end of the arm or beam is larger and more rounded than the first end and a double cut is provided in the fork-like gripping end portion to improve an elasticity of a gripping structure.

28. The orthopaedic surgical instrument according to claim 26, wherein said longitudinal slot is elongated and provided along the structure of the arm or beam for substantially two thirds of its length starting in proximity of the first end.

29. The orthopaedic surgical instrument according to claim 16, wherein said arm or beam has one end hinged to the proximal end of the supporting rod between a terminal stopper and a slidable element slidably mounted in proximity of said proximal end of said supporting rod and configured for being pushed toward a proximal direction by said mechanical switch of the locking device, thus compressing the one end of said arm or beam.

30. The orthopaedic surgical instrument according to claim 29, wherein said slidable element is a bottom wall of a cylindrical sleeve or reversed cup that is in contact with and slidably mounted on an enlarged portion of said proximal end of said supporting rod and having a central hole allowing passing of a top cylindrical portion of the proximal end of said supporting rod.

* * * * *